US005125919A

United States Patent [19]

Miller et al.

[11] Patent Number: 5,125,919

[45] Date of Patent: Jun. 30, 1992

[54] WEDGE-SHAPED PORT FOR FLEXIBLE CONTAINERS

[75] Inventors: Robert A. Miller, Crystal Lake, Ill.; R. Daniel Webster, Sunnyvale; Bradley H. Buchanan, San Francisco, both of Calif.

[73] Assignee: Clintec Nutrition Company, Deerfield, Ill.

[21] Appl. No.: 604,338

[22] Filed: Oct. 24, 1990

Related U.S. Application Data

[63] Continuation of Ser. No. 238,699, Aug. 13, 1988, abandoned.

[51] Int. Cl.[5] .......... A61B 19/00

[52] U.S. Cl. .......... 604/408; 604/415; 215/247; 222/107; 383/42

[58] Field of Search .......... 604/262, 322, 323, 326, 604/403, 407–415, 905; 128/DIG. 24; 206/828; 215/247, 249; 383/42, 44, 46, 53, 54, 67, 78, 84, 86; 222/96, 107

[56] References Cited

U.S. PATENT DOCUMENTS

| | | | |
|---|---|---|---|
| 356,544 | 1/1887 | Parker | 604/408 |
| 2,698,619 | 1/1955 | Beacham et al. . | |
| 2,949,712 | 8/1960 | Bieberdorf . | |
| 3,030,952 | 4/1962 | Elder et al. . | |
| 3,177,870 | 4/1965 | Salem et al. . | |
| 3,968,195 | 7/1976 | Bishop | 604/410 |
| 3,991,912 | 11/1976 | Soto . | |
| 4,078,699 | 3/1978 | Soto . | |
| 4,187,893 | 2/1980 | Bujan | 604/408 |
| 4,202,334 | 5/1980 | Elson | 604/415 |
| 4,230,115 | 10/1980 | Walz, Jr. et al. | 128/DIG. 24 |
| 4,305,443 | 12/1981 | Bayham | 128/DIG. 24 |
| 4,484,916 | 11/1984 | McPhee | 604/415 |
| 4,516,977 | 5/1985 | Herbert | 128/DIG. 24 |
| 4,637,934 | 1/1987 | White | 604/415 |
| 4,723,956 | 2/1988 | Schnell et al. . | |
| 4,732,299 | 3/1988 | Hoyt | 222/94 |

FOREIGN PATENT DOCUMENTS

| | | |
|---|---|---|
| 399297 | 11/1960 | Fed. Rep. of Germany . |
| 1104359 | 7/1966 | United Kingdom . |

OTHER PUBLICATIONS

Entri-Pak, Enteral Feeding System, 1 Liter, Biosearch Medical Products, Inc., Somerville, New Jersey 08876 (no date).

McGaw 5% Dextrose, Inj. Usp. 50 ml Partial Fill, American McGaw, Irvine, California (no date).

I. M. Anderson—Intasept—aseptic Integrity in bag-in-box packaging. Food Technology in Australia—vol. 37(9) Sep. 1985.

*Primary Examiner*—Stephen C. Pellegrino
*Assistant Examiner*—Ralph A. Lewis
*Attorney, Agent, or Firm*—Hill, Van Santen, Steadman & Simpson

[57] ABSTRACT

A wedge-shaped access port for a flexible container is described. The flexible container is formed of at least one or more sheets of material which are sealed together about the edges to form a cavity. The wedge-shaped port is sealed to the container so that a base of the wedge is exterior to the cavity and a thin edge of the wedge is located inside the cavity. An orifice in the port provides a passageway from the base of the wedge to the cavity. The wedge shape of the port allows sealing of the port to container with minimal stress or thinning of material at the seal between the port and the container.

20 Claims, 4 Drawing Sheets

WEDGE-SHAPED PORT FOR FLEXIBLE CONTAINERS

This is a continuation, of application Ser. No. 238,699 filed Sep. 13, 1988 now abandoned.

BACKGROUND OF THE INVENTION

The invention generally relates to ports for containers and more specifically relates to wedge-shaped ports for flexible containers.

It is common medical practice to provide fluids to a patient either intravenously or enterally as a method of treating a patient for various medical conditions. Frequently, the fluids to be administered to a patient are contained in a flexible container. One method of forming a flexible container is to seal two sheets of flexible material about the periphery of the sheets to create a cavity. A port is frequently placed between the sheets during the sealing process to create a communication between the cavity and the exterior of the container to provide a means of introducing fluid into or dispensing fluid from the container. In many cases, a length of flexible tubing is typically attached to this port so that a needle or enteral feeding tube can then be attached to the other end of the tube to administer the fluid to the patient.

Generally speaking, fluids that are administered to a patient must be sterile. Therefore, it is very important that a hermatic seal is created between the port and the container. Certain medical solutions that are administered to patients such as high concentrations of dextrose, amino acids, lipid emulsions, or enteral diets are also oxygen sensitive. Therefore, in those cases, it is also very important that the container and the port are manufactured from materials that reduce permeability of the container, or as an alternative, an overwrap is placed over the container at the time of manufacture to reduce permeability of the container.

Typically fluids to be administered to a patient are added to a flexible container through the use of an access port into the container. A separate port is frequently provided to administer the fluid to the patient. In the past, these ports have been typically formed by placing a tube in between the sheets of the container as the container is manufactured. The tubes are sealed to both sheets of the container during manufacture. Since the tubes have a cylindrical shape and the sheets are basically flat, stresses and thinning occur in the sheets as the sheets are sealed about each tubular port. One means of reducing the stresses created by sealing a tubular port to the sheets of a flexible container is to design the port to have an lenticular rather than cylindrical configuration.

One problem with each of the examples described above, however, is that thinning and stressing of the sheets continues to occur as the flat sheets are forced to seal about a curved port. As long as the material used to create the container is fairly elastic and capable of withstanding stresses, then it is possible to develop an adequate seal between a curved port and a flat sheet. However, in many cases, it is desired to use materials which are relatively inelastic or are very thin and thus more susceptible to stress fractures at the location of the seal of the material to the curved port.

SUMMARY OF THE INVENTION

In view of the foregoing, it is an object of the invention to provide a port having relatively flat surfaces for sealing to a flexible container.

It is another object of the invention to provide a port which has relatively low oxygen permeability.

It is a further object of the invention to provide a port for a flexible container which is relatively easy and inexpensive to manufacture.

It is yet a further object of the invention to provide a port for sealing engagement with a flexible container which minimizes stresses and thinning of the container at the location of sealing between the container and the port.

It is also an object of the invention to provide a plurality of ports for use with a flexible container to provide at least one port for for filling the container and at least one other port for dispensing fluids from the container.

The invention can be briefly described as a container formed from one or more sheets of material and having a seal formed about the periphery to form a cavity. The invention further includes a port in communication with the cavity of the container. The port has a wedge shape with at least one orifice therethrough. The wedge includes a base and first and second oppositely disposed substantially flat sides with extend from the base. The first and second sides form an acute angle. The port includes an orifice that forms a passageway from the base toward the acute angle into the cavity of the container. The port is located between the sheets of material along the seal so that the port is in sealed engagement with the material. The port is disposed in the container such that the acute angle is located within the cavity of the container and the base is located outside the cavity.

DETAILED DESCRIPTION OF THE PREFERRED EMBODIMENT

Figure 1:
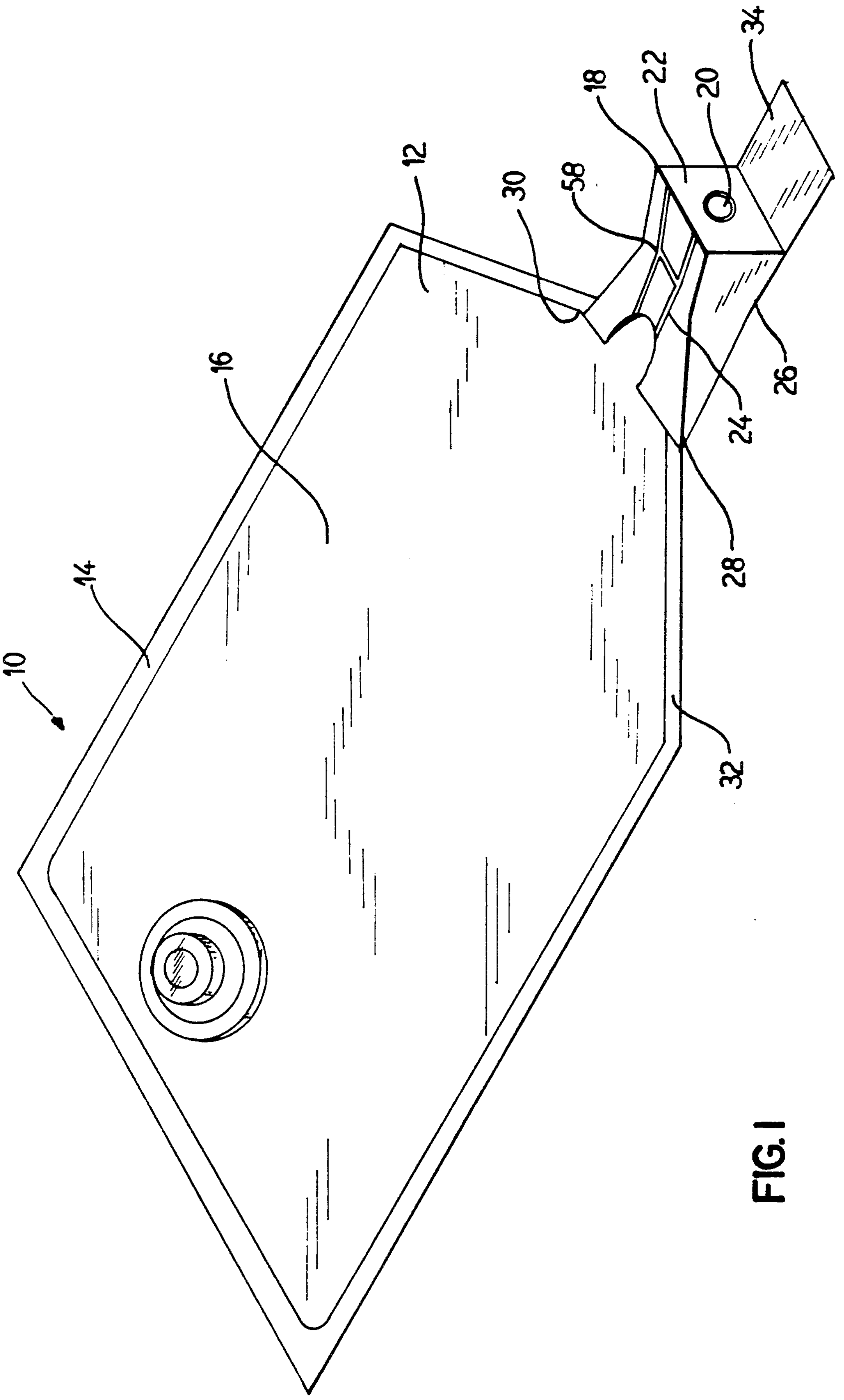
FIG. 1 is an isometric drawing of one embodiment of the invention as sealed within a container.

Referring now to FIG. 1, a flexible container 10 is formed of at least one sheet of flexible material 12. The container is sealed about the edges 14 of the material to form a cavity 16 within the container. A wedge shaped port 18 is located at the bottom of the container. The wedge shaped port has at least one orifice 20 therethrough. The wedge includes a base 22 and first and second oppositely disposed substantially flat sides 24 and 26 extending therefrom. The first and second sides form a generally acute angle 28 which creates a relatively thin edge 30 along the top of the wedge. In a preferred embodiment of the invention, the port is located between the first and second sheets of material 14 and 16 along a seal line 32. The port is disposed in the container such that the acute angle 28 is located within the cavity of the container and the base 22 is located outside of the cavity.

In a preferred embodiment of the invention, at least one sheet of the container may extend downwardly from the base of the wedge to form a flap 34 to cover the orifice 20 at the base 22. The flap may be removably sealed to the base 22 of the wedge 18. In the embodiment illustrated in FIG. 2, a flap 36 may include a first portion 38 which covers the base of the wedge 18 and a second portion 40 which can be folded up over a side 24 of the wedge 18. In many embodiments of the invention, it is desirable for the flap to be temporarily sealed to the base of the wedge 18 in order to maintain cleanliness or sterility of the orifice or to control permeability. In such embodiments, when a user wishes to insert a tube into the port to either add or remove fluid from the container, the user can simply peal back the flap from the port immediately prior to insertion of the tube. In other embodiments, the cover may be formed of an elastomeric resealable material.

Figure 2:
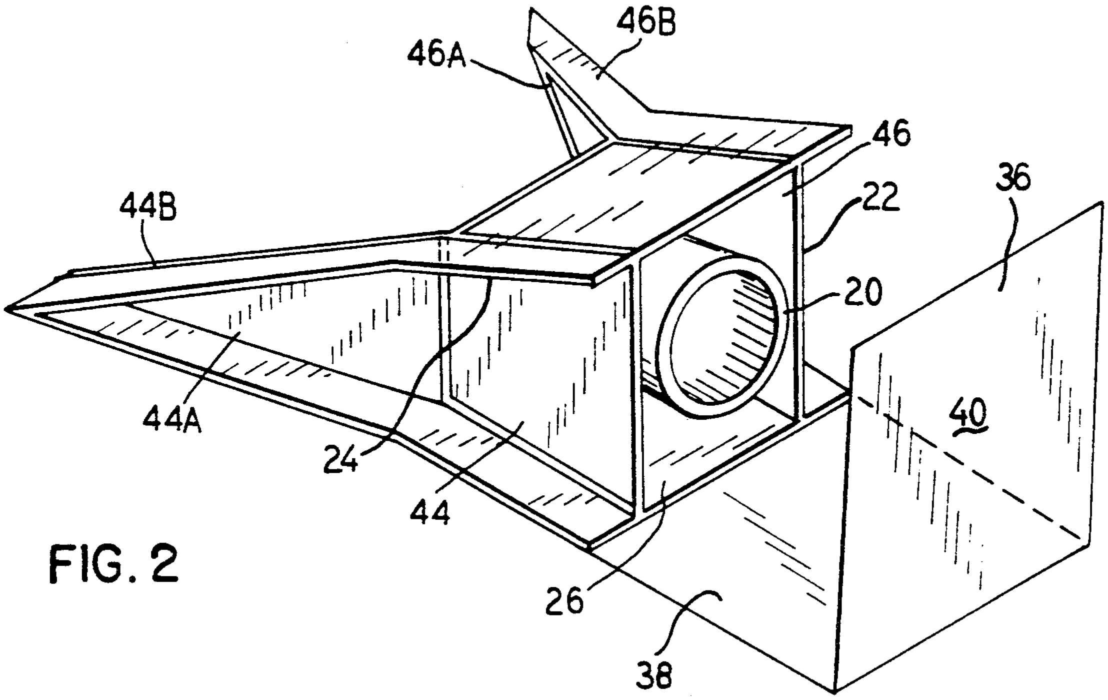
FIG. 2 is an isometric view of a wedge-shaped port including a flap.

In another embodiment of the invention, it may be desirable to permanently seal flap 34 as illustrated in FIG. 1 (or flap 36 as illustrated in FIG. 2) to the base or side wall of the wedge-shaped port. In this embodiment, the flap forms a penetratable membrane which can be ruptured by the user through the use of a spiked tube or needle.

Figure 3:
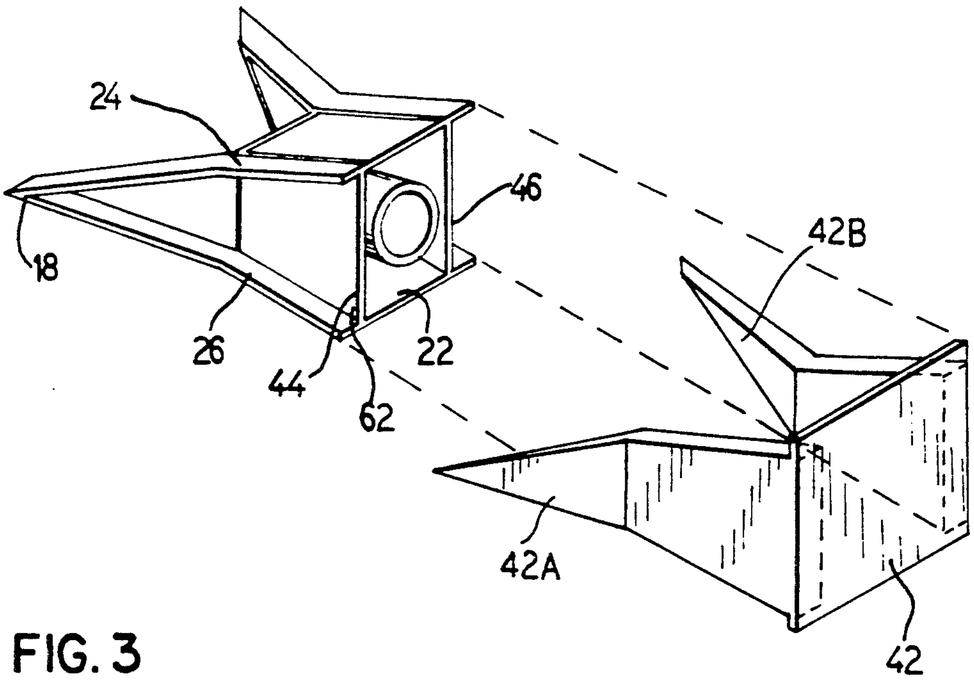
FIG. 3 is an isometric view of a port including a removable cover.

In yet another embodiment of the invention, the port 18 may include a removable cover 42 as illustrated in FIG. 3. As can be seen in the figure, the removable cover 42 covers the base 22 of the wedge 18 and third and fourth side walls 44 and 46 of the wedge. The sidewalls 44 and 46 preferably include two triangular portions 44A and 46A that taper in conformity with the angle 28 and that are outwardly bent so as to extend from the [base 22] sidewalls 44 and 46, respectively, and to define an angle therebetween. Sidewalls 42A and 42B of the cover would thus conform in shape to the sidewalls 44 and 46 and their respective outwardly bent portions 44A and 46A. In one embodiment of the invention, the removable cover can include an adhesive coating to create a temporary bond between the cover and the base of the wedge. This insures that the removable cover will stay on the wedge-shaped port until the user wishes to remove the cover to either introduce fluids or remove fluids from the container.

Figure 4:
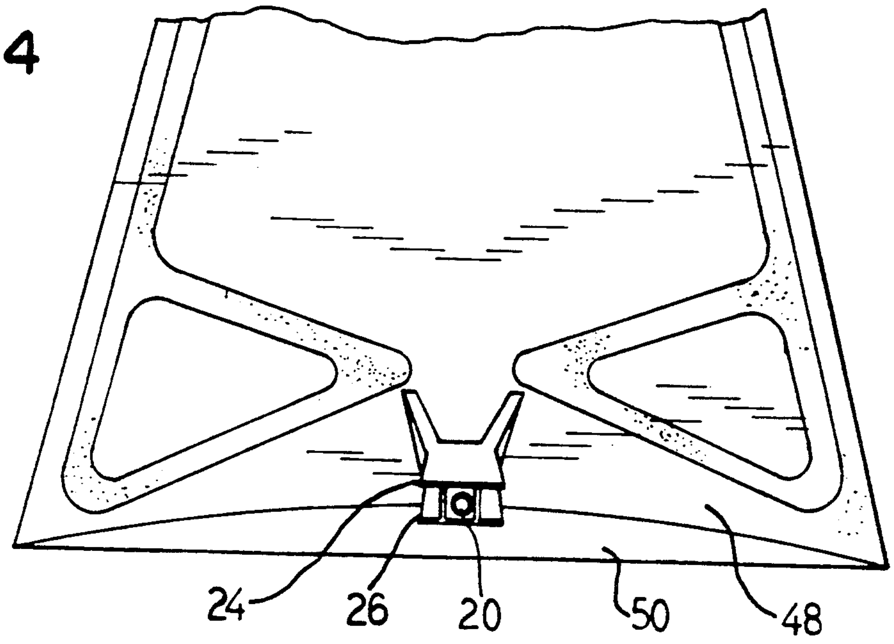
FIG. 4 is an isometric view of a port in which the material forming the container extends beyond the base of the port.
Figure 5:
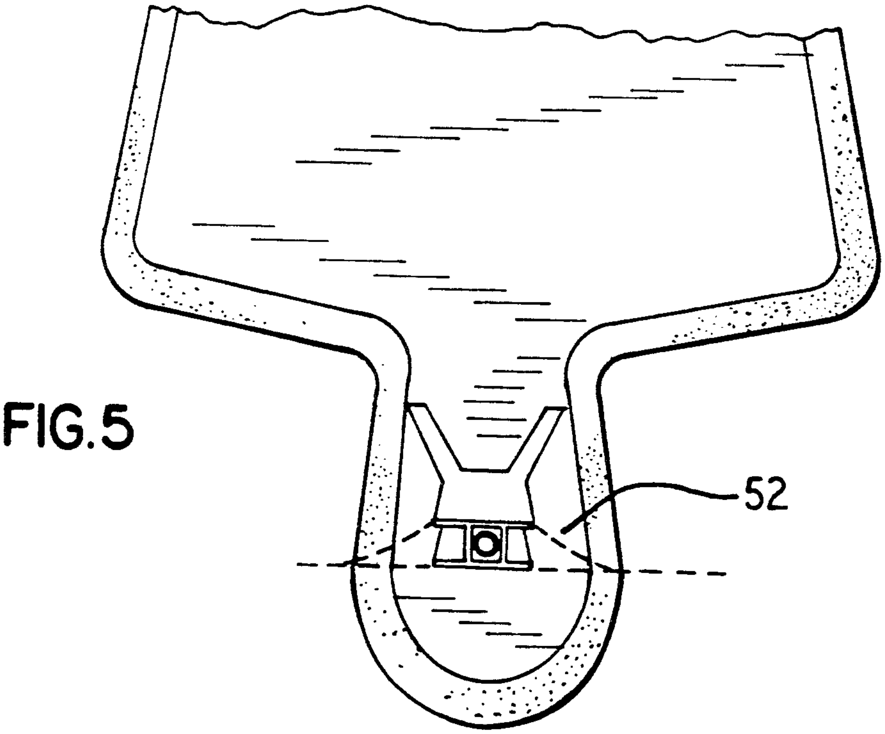
FIG. 5 is a top view, partially broken away, of a wedge-shaped port having a breakable seal surrounding the base of the wedge.

In another embodiment of the invention as illustrated in FIG. 4, the container may include extensions 48 and 50 which extend beyond the base of the wedge-shaped port from each side 24 and 26 of the wedge. It may be desirable to include such extensions 48 and 50 to provide protection for a spike or needle which may be inserted into the port. It may also be desirable to include such extensions on both sides of the wedge to create a sealed enclosure 52 about the base of the wedge as illustrated in FIG. 5.

Figure 6:
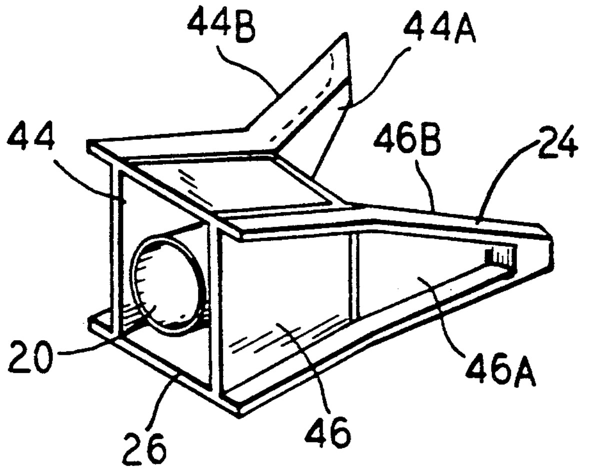
FIG. 6 is an isometric view of a "U-shaped" embodiment of the port of the subject invention.

The side walls 24 and 26 may be generally solid walls as illustrated in FIG. 1 or may be generally "U-shaped" walls as illustrated in FIG. 6 defining two triangular or substantially triangular legs 44B and 46B comprising portions of the sides 24 and 26 and the triangular or substantially triangular extensions 44A and 46A, respectively. The size and thickness of the side walls will, of course, vary depending on the size of the container and the application for which the container is being used. However, generally speaking, it is desirable that the third and fourth side walls 44 and 46 be somewhat thicker than the first and second side walls 24 and 26 when it is desired to minimize oxygen ingress into the cavity of the container. In the preferred embodiment of the invention, the first and second walls will generally be from 0.001 to 1.0 inches thick and the third and fourth walls will generally be from 0.001 to 1.0 inches thick.

The acute angle 28 may likewise vary depending on the use and size of the container or the size of any spiking device that may be used with the container. In general, however, it is preferable that the acute angle range from 1 to 89 degrees.

The wedge-shaped port can be formed from a variety of materials. In general, the main requirement for the material from which the port is formed is that it is capable of forming a hermatic seal with the material from which the container is made. In many embodiments, it is preferable that the port be formed from a material which has low permeability to oxygen and is sterilizable using standard sterilization techniques. Some of the preferred materials to use for the port are polyethylene, polypropylene or polyolefin or any of the materials listed above blended with ethylene vinyl alcohol, polyvinylidene chloride, or nylon. In one embodiment of the invention, it may be desirable to provide a metalized coating on the third and fourth walls 44 and 46 of the port to further reduce permeability of those walls.

In another embodiment of the invention, the orifice 20 may include a membrane 58 which extends across the entire orifice as illustrated in FIG. 1 to form a piercable seal. The membrane creates a barrier between the cavity of the container and the exterior to maintain the cleanliness (or sterility) of the contents of the container prior to use. The membrane also prevents the fluids from leaking from the container.

Figure 7:
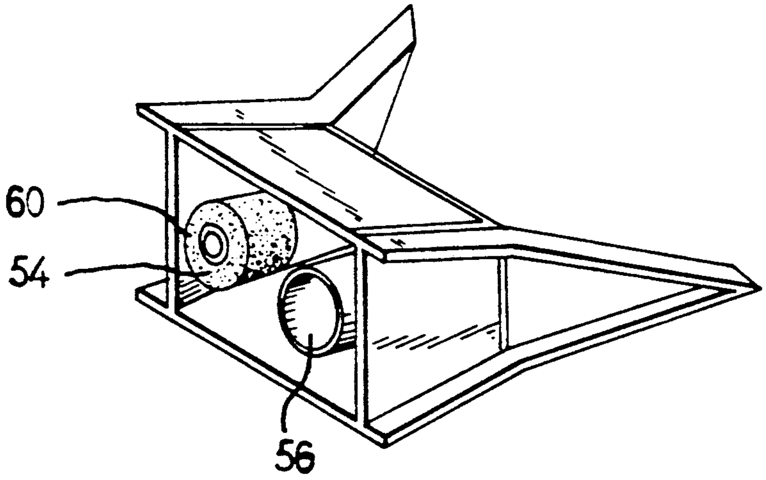
FIG. 7 is an embodiment of the invention containing a plurality of orifices in a wedge-shaped port.

In still yet another embodiment of the invention, the wedge-shaped port may include multiple orifices 54 and 56 as illustrated in FIG. 7. In another embodiment of the invention each orifice may include a conduit 60 which extends beyond the base of the orifice 54 as also illustrated in FIG. 7. The conduit may serve several purposes, for instance, the conduit may support a spike inserted in the port. The conduit may also provide a location for attaching a piercable medication membrane or sterility cover. The conduit may also be useful for attaching flexible tubing to the port.

As can be seen in FIG. 3, in one embodiment of the invention the first and second sides 24 and 26 may extend beyond the third and fourth sides 44 and 46 to create a channel 62 on either side of the wedge shaped port. This channel may be useful as a means for conveying the wedge-shaped port during manufacture of the container.

Figure 8:
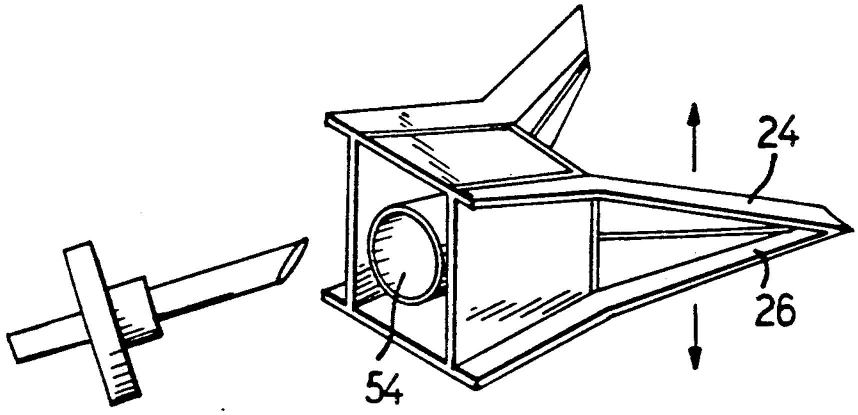
FIG. 8 illustrates an embodiment of the invention in which opposite sides of a wedge-shaped port may flex outwardly.

Referring now to FIG. 8, in another embodiment of the invention the first and second side walls 24 and 26 may be in parallel juxtaposition with each other. As a spike is inserted into the orifice 54 of the port, the side walls 24 and 26 will flex outwardly. This embodiment is desirable to promote complete drainage of fluid from the container because the outward flexure of the side walls also causes the walls of the container to separate from one another to allow fluid to more readily flow into the port.

Although the invention has been described and illustrated in detail, it is to be clearly understood that the same is by way of illustration and example only, and is not to be taken by way of limitation; the spirit and scope of this invention being limited only by the terms of the appended claims.

We claim:

1. A container formed of at least one sheet of material and having a seal operatively formed between two edges of said material to form a cavity for housing a fluid, the invention comprising:

a wedge-shaped port in sealed engagement with said edges of the container, said port having a base and first and second opposing discrete sides which extend from said base, said first and second sides extending from opposite lateral edges of said base, said sides defining two intersecting planes, said intersecting planes describing an acute angle, said port having an orifice extending through said base to provide continuous fluid communication between inside and outside of said cavity, said port being disposed along said edges of said container so that a periphery of said port is inside the cavity while an outer surface of said base is outside of the container, a vertex of the acute angle defined by said intersecting planes being positioned within said cavity, said orifice being so constructed and arranged that a member inserted through said orifice need not penetrate said seal, said port including third and fourth sides attached on other opposite lateral edges of said base, said third and fourth sides having portions that are outwardly bent and that extend beyond said first and second sides so as to form triangular legs whose edges are sealed to said material, said third and fourth sides being tapered in conformity with said acute angle defined by said intersecting planes.

2. A container as recited in claim 1 wherein said first and second sides are from 0.001 to 1.0 inches thick and said third and fourth sides are from 0.001 to 1.0 inches thick.

3. A container formed of at least one sheet of material and having a seal operatively formed between two edges of said material to form a cavity for housing a fluid, the invention comprising:

a port in communication with said container, said port having a wedge shape with at least one orifice therethrough, said port including a base and first and second oppositely disposed substantially flat sides extending therefrom, said first and second sides defining intersecting planes that define said wedge shape, said intersecting planes defining an acute angle, the orifice extending through the base, said port further including third and fourth opposing sides extending from the base, said port being located between said material along said seal and in sealed engagement with said material, said port being disposed in said container such that at least portions of said first and second sides are disposed in said cavity of said container and said base is outside of said cavity, a vertex of said acute angle defined by said intersecting planes being positioned within said cavity, said orifice extending through said port and so constructed and arranged that a member inserted through said orifice need not penetrate said seal, said third and fourth sides extending from, said third and fourth sides being tapered in conformity with said acute angle defined by said intersecting planes, said third and fourth sides having portions outwardly bent and extending to form triangular legs.

4. A container as recited in claim 3 wherein said acute angle ranges from 1 to 89 degrees.

5. A container as recited in claim 3 wherein said orifice includes a membrane to form a piercable seal across said orifice.

6. A container as recited in claim 3 further including:

at least one conduit extending from at least one of said orifices.

7. A container as recited in claim 3 wherein said first and second opposing sides are so constructed and arranged that they flex outwardly when a spike is inserted into said cavity through said orifice.

8. A container as recited in claim 3, further comprising a removable cover surrounding said base and said third and fourth sides, said removable cover being formed from a material having low permeability.

9. A container as recited in claim 3 wherein said third and fourth sides have outer surfaces with a coating to control permeability of the port.

10. A container as recited in claim 3 wherein at least one side of said material extends beyond said base of said port to form a flap to cover said orifice at said base.

11. A container as recited in claim 10 wherein said third and fourth sides have outer surfaces with a coating means for controlling the permeability of the port.

12. A container as recited in claim 3 which further includes:

a removable cover which covers said base.

13. A container as recited in claim 12 wherein said removable cover further covers said third and fourth sides.

14. A container as recited in claim 13 wherein said removable cover includes an adhesive coating for removably attachment of said cover to said base.

15. A container as recited in claim 13 wherein said removable cover is formed of an elastomeric resealable material.

16. A container formed of at least one sheet of material and operatively having a seal formed around opposite edges of the material to form a cavity, comprising:

a port in communication with the container including a substantially rectangular member having an opening therethrough, and first, second, third and fourth sides attached thereto, the first and second sides being attached at opposite lateral edges of the member and defining two intersecting planes that define a wedge shape with a vertex positioned within the cavity, an orifice member extending from the rectangular member to provide fluid communication between the cavity and an exterior of the container, the vertex being positioned such that a member inserted through the orifice member need not penetrate the container seal, the third and fourth sides being attached at remaining opposite lateral edges of the member and between the first and second sides, the sides and the member forming a substantially frustrum shaped enclosure having one open face opposite the member, a periphery of the sides forming the open face defining a base, the third and fourth sides extending beyond the member toward the vertex to describe two extending members, the port being located between edges of the material along the seal and being in sealing engagement therewith, the base being located outside the cavity, the open side of the enclosure facing away from the cavity.

17. The container of claim 16 wherein the extending members formed by the third and fourth sides are substantially triangular in shape having a taper that follows the wedge shape defined by the planes defined by the first and second sides.

18. The container of claim 17 wherein the third and fourth sides have a substantially truncated triangular cross-sectional shape.

19. An enclosure port member, comprising:

a substantially rectangular member with at least one opening;

a tubular conduit operatively extending in registry from said opening in said rectangular member;

two sides having outwardly flaring triangular portions attached to opposite lateral edges of said rectangular member, the outwardly flaring portions being tapered to define a wedge with an acute angle that opens toward said rectangular member; and two other sides attached on other opposite lateral edges of the rectangular member and along a portion of a periphery of said triangular sides to provide a wedge the four sides and the rectangular member defining a frustrum-shaped body which surrounds said conduit.

20. A port for a container, comprising:

a frustrum-shaped body that substantially encloses a space, first and second faces describing first and second sides of said port, third and fourth faces describing third and fourth sides of said port, said third and fourth sides being tapered so as to impart a wedge shape to said port, and said first and second sides defining intersecting planes in accordance with said wedge shape, a rectangular member positioned and secured to form a top of said body, the rectangular member including at least one port opening, said third and fourth sides having portions extending beyond said rectangular member to define two extending triangular members, and a conduit extending from said port opening in a direction opposite said extending triangular members.

* * * * *